(12) United States Patent
Rajaiah et al.

(10) Patent No.: US 6,617,374 B1
(45) Date of Patent: Sep. 9, 2003

(54) DENTURE ADHESIVES WITH MIXED SALTS OF ALKYL VINYL ETHER-MALEIC COPOLYMER OR TERPOLYMER

(75) Inventors: Jayanth Rajaiah, Loveland; Carole Ann Schumacher, Cincinnati; John Roy Whitney, Hamilton; Kimberly Ann Gilday-Weber; Robert Hargitt Culbertson, both of Cincinnati, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/389,209

(22) Filed: Sep. 2, 1999

Related U.S. Application Data

(63) Continuation-in-part of application No. 09/291,554, filed on Apr. 14, 1999.

(51) Int. Cl.[7] .............................................. A61C 13/23
(52) U.S. Cl. ......................... 523/120; 526/272; 106/35
(58) Field of Search .................... 523/120; 106/35; 526/272

(56) References Cited

U.S. PATENT DOCUMENTS

| | | | | |
|---|---|---|---|---|
| 3,003,988 A | | 10/1961 | Germann et al. | 106/35 |
| 3,736,274 A | | 5/1973 | Schoenholz et al. | 524/45 |
| 4,503,116 A | | 3/1985 | Lapidus | 428/286 |
| 4,514,528 A | | 4/1985 | Dhabhar et al. | 523/120 |
| 4,632,880 A | | 12/1986 | Lapidus | 428/523 |
| 4,758,630 A | | 7/1988 | Shah et al. | 525/207 |
| 4,910,247 A | | 3/1990 | Haldar et al. | 524/400 |
| 5,037,924 A | | 8/1991 | Tazi et al. | 526/272 |
| 5,073,604 A | | 12/1991 | Holeva et al. | 525/327.8 |
| 5,082,913 A | | 1/1992 | Tazi et al. | 526/272 |
| 5,204,414 A | | 4/1993 | Pelah et al. | 525/327.8 |
| 5,298,534 A | * | 3/1994 | Prosise et al. | 523/120 |
| 5,304,616 A | | 4/1994 | Rajaiah et al. | 526/240 |
| 5,369,145 A | | 11/1994 | Gasman et al. | 523/120 |
| 5,395,867 A | * | 3/1995 | Prosise | 523/120 |
| 5,424,058 A | | 6/1995 | Rajaiah et al. | 424/49 |
| 5,525,652 A | | 6/1996 | Clarke et al. | 524/37 |
| 5,696,181 A | * | 12/1997 | Chang et al. | 523/120 |
| 5,750,591 A | | 5/1998 | Clarke et al. | 523/120 |
| 5,830,933 A | | 11/1998 | Synodis et al. | 524/37 |
| 5,872,160 A | * | 2/1999 | Liang et al. | 523/120 |
| 5,872,161 A | | 2/1999 | Liang et al. | 523/120 |
| 5,877,233 A | * | 3/1999 | Liang et al. | 523/120 |
| 5,880,172 A | * | 3/1999 | Rajaiah et al. | 523/120 |
| 5,900,470 A | | 5/1999 | Prosise et al. | 526/272 |
| 6,069,188 A | * | 5/2000 | Rajaiah et al. | 523/120 |

FOREIGN PATENT DOCUMENTS

| | | | |
|---|---|---|---|
| EP | 0 265 916 A2 | 5/1988 | ............ A61K/6/00 |
| WO | WO 92/10988 | 7/1992 | ............ A61K/6/00 |
| WO | WO 96/04883 | 2/1996 | ........... A61K/6/087 |
| WO | WO 96/13243 | 5/1996 | ............ A61K/6/00 |
| WO | WO 97/10772 | 3/1997 | |
| WO | WO 98/43595 | 10/1998 | |
| WO | WO 99/18140 | 4/1999 | ......... C08F/222/04 |
| WO | WO 00/33792 | 6/2000 | |

* cited by examiner

*Primary Examiner*—Peter Szekely
(74) *Attorney, Agent, or Firm*—Betty J. Zea

(57) ABSTRACT

The present invention relates to a denture adhesive composition comprising mixed salts of an alkyl vinyl ether-maleic acid or anhydride copolymer and/or terpolymer with isobutylene wherein the mixed salt contains a cationic salt function comprising at least about 22.5% calcium cations, from about 15% to about 25% of zinc cations, of the total initial carboxyl groups reacted, the mixed salt containing from about 36% to about 50% free acid component. In addition the present invention relates to denture adhesive compositions comprising the above composition and at least one non-adhesive self-supporting layer. The present invention further relates to a method of increasing the adhesion of dentures to the oral cavity by applying the above compositions to dentures, directly to the oral cavity, palate or ridge of the oral cavity, or applying it to both, and thereafter securing the denture to the ridge or palate of the oral cavity.

9 Claims, No Drawings

DENTURE ADHESIVES WITH MIXED SALTS OF ALKYL VINYL ETHER-MALEIC COPOLYMER OR TERPOLYMER

This application is a continuation-in-part of U.S. Copending application Ser. No. 09/291,554 filed on Apr. 14, 1999.

BACKGROUND OF THE INVENTION

Ordinary removable dentures, dental plates and the like, comprise teeth mounted in a suitable plate or base. Denture stabilizers are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Considerable effort has been made over the years to develop improved denture adhesive compositions. Both synthetic and natural polymers and gums have been used singly, in combination, and in combination with various adhesives and other materials in an attempt to lessen certain deficiencies. These deficiencies include inadequate holding power, oozing of the adhesive from under the dental plate during insertion and throughout the wearing period, and messiness and difficulty of removing the residual adhesive from the mouth and dentures. Additionally, food may become trapped between the denture and the oral cavity of the wearer.

Alkyl vinyl ether-maleic copolymers and salts thereof are known in the art for use in denture adhesive compositions. Such disclosures include: U.S. Pat. No. 3,003,988 to Germann et al., issued Oct. 10, 1961; U.S. Pat. No. 4,980,391 to Kumar et al., issued Dec. 25, 1990; U.S. Pat. No. 5,073,604 to Holeva et al., issued Dec. 17, 1991; U.S. Pat. No. 5,900,470, Prosise et al., issued May 4, 1999; U.S. Pat. No. 5,037,924, Tazi et al, issued Aug. 6, 1991; U.S. Pat. No. 5,082,913, Tazi et al., issued Jan. 21, 1992; and U.S. Pat. No. 5,525,652 to Clarke, issued Jun. 11, 1996. In addition strip or insert denture adhesives are also known. For example, U.S. Pat. No. 4,880,702 to Homan et al., issued Nov. 14, 1989 discloses a denture stabilizer in the form of a strip consisting of three layers. The two outside layers consist of a polymer selected from the group consisting of polyethylene oxide having an average molecular weight of about 200,000 to 10,000,000, sodium carboxymethylcellulose, polyvinyl alcohol, and mixtures thereof. The inside layer consists of microcrystalline wax and a polymer sufficient to adhere the inside layer to gums and a denture base, after contact with water, when the outside layers have been dissolved. European Patent Application 0,353,375 to Altwirth published Feb. 7, 1990, discloses an adhesive insert for dentures consisting of a adhesive permeated fibrous fleece and an adhesive consisting of a pasty mixture of alginate and/or carboxymethylcellulose, polyvinyl acetate and an alcoholic solvent. Despite the above-noted technologies as well as many others, a need still exists for denture stabilizing compositions providing improved hold.

In accordance with the present invention, it has been discovered that denture adhesive compositions comprising alkyl vinyl ether-maleic acid copolymers and/or terpolymers with isobutylene comprising calcium and zinc mixed salts together with specific levels of free acid provide superior denture hold. The present denture adhesive compositions may also be effectively used as a wound dressing, underwater adhesive, a bioadhesive, a delivery vehicle for other actives, and/or any other application that requires adhesion to skin or tissue, including cosmetic pore cleansing strips.

An object of the present invention is to provide alkyl vinyl ether-maleic copolymers and/or terpolymers comprising calcium and zinc mixed salts, together with specific levels of free acid for adhesive compositions for firm hold, which may be used with dentures. These composition effectively hold dentures in place for a prolonged period of time.

SUMMARY OF THE INVENTION

The present invention relates to a denture adhesive composition comprising mixed salts of an alkyl vinyl ether-maleic acid copolymer and/or terpolymer with isobutylene wherein the mixed salt contains a cationic salt function comprising, or in the alternative consists essentially of, at least about 22.5% calcium cations, from about 15% to about 25% of zinc cations, from 0% to about 2.5% of a cation selected from the group consisting of iron, boron, aluminum, vanadium, chromium, manganese, nickel, copper, yttrium, titanium, and mixtures thereof, of the total initial carboxyl groups reacted, the mixed salt containing from about 36% to about 50% free acid component. In addition the present invention relates to denture adhesive compositions comprising the above composition and at least one non-adhesive self-supporting layer. The present denture adhesive compositions can optionally comprise one or more additional adhesive components. The present invention further relates to a method of increasing the adhesion of dentures to the oral cavity by applying the above compositions to dentures, directly to the oral cavity, palate or ridge of the oral cavity, or applying it to both, and thereafter securing the denture to the ridge or palate of the oral cavity.

DETAILED DESCRIPTION OF THE INVENTION

The denture adhesive compositions of the present invention comprise calcium and zinc mixed salts of an alkyl vinyl ether-maleic copolymer and/or terpolymer with isobutylene (preferably copolymers) with specific free acid levels, and optionally comprising from 0% to about 2.5% of a cation selected from the group consisting of iron, boron, aluminum, vanadium, chromium, manganese, nickel, copper, yttrium, titanium, and mixtures thereof. The adhesive compositions may be in the form of a powder, cream, paste, liquid, aerosol, and/or wafer. Powder forms are sprinkled on a dental prosthesis, moistened and then inserted into the oral cavity. The compositions may also be combined with various conventional delivery vehicles to form liquids or pastes which are applied to a dental prosthesis and inserted into the oral cavity. These compositions can optionally comprise at least one non-adhesive self-supporting layer. Denture adhesive compositions with a self-supporting layer are thoroughly moistened and applied to dentures. A detailed description of essential and optional components of the present invention is given below.

Definitions

The term "safe and effective adhesive amounts" as used herein means an amount sufficient to provide adherence to the oral cavity and/or adherence of a dental prosthesis to the palate and ridge of the oral cavity, without toxicity to the user, damage to oral tissue, and alteration of the denture material.

The term "AVE/MA" as used herein refers to alkyl vinyl ether-maleic acid copolymer. The term "AVE/MA/IB" refers to terpolymers with alkyl vinyl ether, maleic acid, and isobutylene. The term "mixed polymer salts" or "mixed salts", as used herein, refers to salts of AVE/MA and/or AVE/MA/IB where at least 2 different cations are mixed on the same polymer with each other or with other ester functions. The present invention comprises mixed polymer (copolymer or terpolymer) salts containing as essential salts: zinc and calcium cations. The term "free acid" ("FA") component as used herein refers either to the unreacted carboxyl groups (—COOH) of AVE/MA and/or AVE/MA/IB plus any other monovalent cations of carboxyl groups; e.g., —COONa, of the polymer. Monovalent cations include Group IA cations, such as sodium, potassium, hydrogen, etc. Preferably, the term "free acid" refers to the unreacted carboxyl groups (—COOH) of AVE/MA copolymer and/or AVE/MA/IB, plus sodium and potassium cations. More preferably, the term "free acid" refers only to the unreacted carboxyl groups (—COOH) of AVE/MA and/or AVE/MA/IB. The term "additional adhesive component", as used herein, refers to adhesives other than those described as essential AVE/MA and/or AVE/MA/IB mixed salts of the present invention.

The percentages used herein to describe the mixed salt function of the copolymers or terpolymer are defined as the stoichiometric percent of the total initial carboxyl groups reacted on the polymer. All other percentages used herein are by weight unless otherwise indicated.

Polymer

The alkyl vinyl ether-maleic acid copolymer comprises the repeated structural unit:

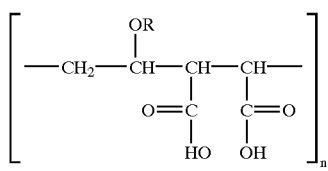

wherein R represents an alkyl radical, preferably a $C_1$ to $C_5$ alkyl radical, n is an integer greater than one representing the number of repeated occurrences of the structural unit in a molecule of the polymer.

The "terpolymer" or "terpolymer with isobutylene" means a terpolymer of maleic anhydride or acid, an alkyl vinyl ether (preferably with a $C_1$–$C_5$ alkyl radical), and isobutylene, having a structure of $(A-B)_n$ where A is maleic anhydride or acid and B is alkyl vinyl ether (preferably with a $C_1$–$C_5$ alkyl radical), and/or isobutylene. The specific viscosity of the starting anhydride or acid of the terpolymer is preferably at least about 5.5, preferably at least about 6, preferably measured as a 1% weight/volume solution of methyl ethyl ketone at 25° C. The terpolymer must contain at least some isobutylene.

The present denture adhesive compositions comprise mixed salts of an AVE/MA copolymer and/or terpolymer wherein the mixed salt contains a cationic salt function comprising (or consisting essentially of) at least about 22.5% calcium cations, from about 15% to about 25% zinc cations, from 0% to about 2.5% of a cation selected from the group consisting of iron, boron, aluminum, vanadium, chromium, manganese, nickel, copper, yttrium, titanium, and mixtures thereof, of the total initial carboxyl groups reacted, the mixed salt containing from about 36% to about 50% free acid component. The AVE/MA copolymers have a range of specific viscosities. For example, the specific viscosity is preferably from 1.2 to 14, as preferably measured as a 1% weight/volume solution of the starting anhydride or acid of the copolymer, in methyl ethyl ketone at 25° C. Other methods and solvents can be used to measure the specific viscosity such as a 1% weight/volume solution in DMF (dimethyl formamide) at 25° C. and a 1% weight/volume solution in 2-butanone at 25° C.

Preferably the cationic salt function contains from about 22.5% to about 49% calcium cations, more preferably from about 23.5% to about 48% calcium cations, of the initial carboxyl groups reacted. In addition, preferably the cationic salt function contains from about 16% to about 24% zinc, more preferably from about 18% to about 22% zinc cations, of the initial carboxyl groups reacted; preferably from about 0.001% to about 2.5% iron cations, more preferably about 0.01% to about 2% iron cations, of the initial carboxyl groups reacted. Preferably the cationic salt function contains from about 37.5% to about 45% free acid component. Preferably the free acid component levels refer only to H+(—COOH).

The alkyl vinyl ether maleic anhydride copolymers are obtained by co-polymerizing an alkyl vinyl ether monomer, such as methyl vinyl ether, ethyl vinyl ether, divinyl ether, propyl vinyl ether and isobutyl vinyl ether, with maleic anhydride to yield the corresponding alkyl vinyl ether-maleic anhydride copolymer which is readily hydrolyzable to the acid copolymer. Suitable copolymers may be prepared by well-known methods of the prior art, for example U.S. Pat. No. 2,782,182, and U.S. Pat. No. 2,047,398, both of which are herein incorporated by reference in their entirety. Both anhydride and acid forms are also available from commercial suppliers. For example, the GAF Corporation, Wayne, N.J. provides both the polymeric free acid form (I) and the corresponding anhydride form under its "GANTREZ" trademark as the "GANTREZ S Series" and "GANTREZ AN Series", respectively. When the anhydride copolymer dissolves in water, the anhydride linkage is cleaved so that the highly polar, polymeric free acid (I) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis. The terpolymers can be made by the methods discussed in U.S. Pat. No. 5,900,470, Prosise et al., issued May 4, 1999; U.S. Pat. No. 5,037,924, Tazi et al., issued Aug. 6, 1991; and U.S. Pat. No. 5,082,913, Tazi et al., issued Jan. 21, 1992, herein incorporated by reference in their entirety.

The salt form of the subject polymers may be prepared by the interaction of the AVE/M anhydride or acid copolymer or terpolymer with at least one cationic salt function, such as zinc, calcium, sodium, potassium, iron, or ammonium compounds having a functional group typical of reactants of a carboxylic acid, such as, for example, the hydroxide, oxide, acetate, halide, lactate, etc. in an aqueous medium. In a preferred embodiment, the zinc oxide and calcium hydroxide are utilized. Mixed polymer salts comprising iron cations can be prepared by the interaction of the AVE/M anhydride/acid polymers with iron compounds, in the form of a salt, such as iron sulfate n-hydrate.

Ions that form toxic, irritating or contaminating by-products should be avoided, or special precautions and treatment provided to assure the removal and absence of such by-products from the polymeric salt end-product. The particular compound used should be substantially pure to assure obtaining a substantially pure, polymeric salt end-product.

If the salt form of the polymer is desired, then an aqueous dispersion of particulate zinc oxide is combined with calcium hydroxide and, optionally, ferric sulfate n-hydrate. This is combined with powder polymer, in the form of a slurry, in an amount sufficient to provide the desire cationic content desired in the end-product. This is done at ambient temperature and then slowly heated to 70°–95° C. with continuous vigorous mixing so as to prevent localized precipitation of the cationic polymeric salt; mixing is continued to ensure that all the salt forming compound is reacted with the copolymer.

Alternatively, the polymer is hydrolyzed and neutralized in an aqueous mixture or slurry of one or more divalent and/or monovalent metal bases by heating the polymer/base mixture to a temperature ranging from about 45° C. to about 100° C. Reaction of the mixed polymer salt with iron cations is obtained through addition of iron salts to the hydrolyzed and neutralized mixed salt of the polymer. Completion of the reaction with iron cations is indicated by an increase in viscosity to stabilization. Alternatively, iron salts may be blended with the polymer/metal base mixture prior to the hydrolysis and neutralization reactions.

In either of the above processes, the resulting slurry or solution is transferred to shallow stainless steel drying trays and placed in a forced air mechanical convection oven at 60–70° C. for a time sufficient to evaporate the reaction medium (water) and remove water from the polymer (about 18–24 hours). Alternatively, the resulting slurry or solution can be drum-dried at 100°to 200° C. with hot steam to evaporate the water content and recover the polymer in the flake form. After drying, the polymer forms brittle flakes which can easily be peeled off from the trays or drum surface and ground to a fine powder as desired to provide satisfactory denture stabilizing properties. Methods of making these mixed salts of AVE/MA polymers are further disclosed in U.S. Pat. No. 5,073,604, Holeva et al., issued Dec. 17, 1991 and U.S. Pat No. 5,872,161, Liang et al., issued Feb. 16, 1999; U.S. Pat. No. 5,830,933, Synodis et al., issued Nov. 3, 1998, all of which are herein incorporated by reference in their entirety.

The mixed salt polymers have exceptional adhesive qualities when contacted with water or saliva such that they are extremely useful as denture adhesive materials in denture compositions. The compositions of the present invention comprise a safe and effective adhesive amounts of the mixed salt polymers, preferably at least 20 percent by weight, and more preferably at least 30 percent by weight of the composition, as the sole adhesive component or as a co-adhesive in joint usage with other adhesive components.

Optional Non-Adhesive Self-Supporting Layer

The present denture adhesive compositions optionally comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include materials such as polyester, polypropylene, nylon, rayon, cellulose acetate, non-adhesive cellulose derivatives, cloth, fibrous fleece, paper, plastic, leather, microcrystalline wax, synthetic fibers, natural fibers, and mixtures thereof. Preferred are non-adhesive cellulose derivatives, polyester, polypropylene, nylon, rayon, cloth, paper, microcrystalline wax, and mixtures thereof. More preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof Other Adhesive Components The present invention compositions may also include other adhesive components. These adhesive components, if present, are used in a safe and effective adhesive amounts. In general, the other adhesive components may be present at a level of from about 0% to about 90%, preferably from about 10% to about 70%, and most preferably from about 20% to about 50%, by weight of the composition.

Suitable adhesive components include a water-soluble hydrophilic colloid or polymer having the property of swelling upon exposure to moisture to form a mucilaginous mass. Such adhesive materials include natural gums, synthetic polymeric gums, AVE/MA copolymer acid, AVE/MA copolymer anhydride, AVE/MA/IB, synthetic polymers, mucoadhesive polymers, hydrophilic polymers, saccharide derivatives, cellulose derivatives, and adhesive materials commonly employed in denture stabilizing compositions and compatible with the subject polymers of the present invention, and mixtures thereof. Examples of such materials include karaya gum, guar gum, gelatin, algin, sodium alginate, tragacanth, chitosan, polyethylene glycol, acrylamide polymers, carbopol, polyvinyl alcohol, polyamines, polyquarternary compounds, polybutenes, silicones, ethylene oxide polymers, polyvinylpyrrolidone, cationic polyacrylamide polymers.

Preferred are cellulose derivatives, polyethylene glycol, polyethylene oxide, karaya gum, sodium alginate, chitosan, polyvinyl alcohol, and mixtures thereof. Most preferred are cellulose derivatives such as methylcellulose, carboxymethylcellulose, hydroxyethylcellulose, hydroxypropylcellulose, hydroxy-propylmethylcellulose, and mixtures thereof.

Other Ingredients

The present invention may also comprise a reducing agent. The reducing agent aids in removal of the denture from the oral cavity after application of the mixed polymer salt of the present invention to the denture. The preferred reducing agent for use herein is ascorbic acid and its water soluble salts. The reducing agent may also be used in combination with a chelating agent. Preferred chelating agents include citrate, tartrate, lactate, and the like. The reducing agent and/or chelating agent may also be delivered in a composition by carriers known in the art which are safe for oral administration (i.e., non-toxic and approved for use in humans). Such carriers include surfactants, solvents, etc.

The reducing agent and/or chelating agents are used in safe and effect amounts. The term "safe and effective amount", as used herein, means an amount sufficient to aid in releasing the denture hold in the oral cavity without toxicity to the user, damage to oral tissue, and alteration of the denture material. Thus, a denture wearer applies the mixed polymer salt adhesive composition to dentures or oral tissue and inserts the denture into the oral cavity. When removal is desired, the wearer swishes in the mouth, a denture releasing composition comprising a reducing agent and/or chelating agents and suitable solvent(s) which aids in releasing the denture hold.

In addition one or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal®, Gafac®, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, preferably from about 1% to about 30%, by weight of the compositions.

The present denture adhesive compositions which also comprise a non-adhesive self-supporting layer may also comprise a coating which is sticky to dry dentures and, if present, will be placed on one side of the denture adhesive composition. Compositions suitable for use as this type of adhesive layer include polybutenes, silicones, rubbers, petrolatum, natural polymers, synthetic polymers, and mixtures thereof. The adhesive layer may be present at a level of from about 0% to about 70%, and preferably from about 0.5% to about 20%, by weight of the composition.

Other suitable ingredients include colorants, preservatives such as methyl and propyl parabens; thickeners such as silicon dioxide, and polyethylene glycol; and vehicles such as liquid petrolatum, petrolatum, mineral oil and glycerin. Preferred are polyethylene glycol, silicon dioxide, and petrolatum. Colorants, preservatives, thickeners and vehicles may be present at levels of from about 0% to about 20%, by weight of the composition.

The compositions of the present invention may also include one or more components which provide flavor, fragrance, and/or sensate benefit (warming or cooling agents). Suitable components include natural or artificial sweetening agents, menthol, menthyl lactate, wintergreen oil, peppermint oil, spearmint oil, leaf alcohol, clove bud oil, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety. These agents may be present at a level of from about 0% to about 50%, by weight of the composition.

The present compositions may be used as a denture adhesive and/or used as a bioadhesive on wet tissue such as mucosal tissues, wounds, oral mucosa, etc. The present adhesive compositions can be used to deliver one or more therapeutic actives suitable for topical administration to mucosal or wet tissues. The phrase "therapeutic actives", as used herein, describes agents which are pharmacologically active when absorbed through wet tissue or mucosal surfaces of the body such as the oral cavity, wounds, or applied to the surfaces of the skin. Therapeutic actives may be present at a level of from about 0% to about 70%, by weight of the composition.

Therapeutic actives that are useful in the present compositions include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; anesthetic agents such as lidocaine or benzocaine; anti-fungals; aromatics such as camphor, eucalyptus oil, flavors, fragrances, or sensates (warming or cooling agents), and aldehyde derivatives such as benzaldehyde; insulin; steroids; and antineoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Process for Preparation of the Composition

A process for preparing denture adhesive compositions of the present invention (creams, powders, wafers, liquids, aerosols, pastes) comprises conventional methods disclosed in the art. Conventional methods are taught in U.S. Pat. No. 5,525,652, issued Jun. 11, 1996, Clarke et al.; U.S. Pat No. 3,003,988, issued Oct. 10, 1961, Germann et al.; U.S. Pat. No. 5,073,604, Holeva et al., issued Dec. 17, 1991; and U.S. Pat. No. 5,872,161, Liang et al., issued Feb. 16, 1999, all of which are herein incorporated by reference in their entirety.

A process for the preparation of the present denture adhesive compositions optionally comprising a non-adhesive self-supporting layer, comprises coating a weighed amount of the adhesive components onto the non-adhesive self-supporting layer. This process is disclosed in U.S. Pat. No. 5,877,233, Liang et al, issued Mar. 2, 1999; U.S. Pat. No. 5,872,160, issued Feb. 16, 1999, Liang et al.; U.S. Pat. No. 5,880,172, Rajaiah et al., filed Oct. 25, 1996, all of which are incorporated herein by reference in their entirety.

The term "mixture", as used in this "Process for Preparation the Composition" section, refers to a solution, slurry, or suspension.

The adhesive components may be coated on the non-adhesive self-supporting layer using various methods. These include: (a) wetting the non-adhesive self-supporting layer with water, uniformly sifting the adhesive component powder(s) onto the wet layer and then rewetting the layer with water; (b) dissolving the adhesive component(s) in water and/or other solvent(s) and coating the resulting mixture on the layer; (c) coating the layer with the mixture produced during AVE/MA polymer processing; (d) incorporating the adhesive component(s) into the layer as the layer is being formed; and (e) dissolving the adhesive component (s) in water and/or other solvent(s), wetting/coating the resulting mixture onto the layer, and uniformly sifting one or more adhesives in powder form onto the wet/coated layer and optionally re-coating/re-wetting the layer with the mixture and/or water; (f) the method of step (e) repeated multiple times; and (g) any combination of the methods in (a) through (f) above.

As disclosed above, the adhesive components may be dissolved in water and/or other solvents and the resulting mixture coated onto the layer. Solvents for the polymers include water and/or alcohols such as methanol, propanol, isopropanol, ethanol, butanol, 1,4-butanediol, cyclohexanol, and diethylene glycol; ethers or ether alcohols such as tetrahydrofuran, ethylene glycol monomethyl ether, diethylene glycol monomethyl ether, dioxane, and ethyl ether; esters such as methyl acetate, ethyl acetate and sec-butyl acetate; aldehydes, ketones or ketone-alcohols such as benzaldehyde, formaldehyde solution, methyl ethyl ketone, diacetone alcohol, acetone, cyclohexanone, mesityl oxide, and methyl isobutyl ketone; lactams or lactones such as N-methyl-2-pyrrolidone, N-vinyl-2-pyrrolidone, 2-pyrrolidone, and butyrolactone; hydrocarbons such as benzene, toluene, xylene, hexane, mineral spirits, mineral oil, and gasoline; chlorinated hydrocarbons such as carbon tetrachloride, chlorobenzene, chloroform, ethylene dichloride, methylene chloride; nitroparaffins such as nitroethane, and nitromethane; mercaptans such as thiophenol and 2-mercapto-1-ethanol; and others such as acetic acid, pyridine and dimethyl formamide.

Preferred solvents for the polymers are water, methanol, propanol, isopropanol, tetrahydrofuran, methyl acetate, benzaldehyde, formaldehyde solution, methyl ethyl ketone, diacetone alcohol, N-methyl-2-pyrrolidone, N-vinyl-2-pyrrolidone, dimethyl formamide and mixtures thereof. Compounds commonly used as plasticizers can also be used as solvents for the polymers. Such plasticizers include dimethyl phthalate, diethyl phthalate, dioctyl phthalate, glycercin, diethylene glycol, triethylene glycol, Igepal® CO-630 (nonyl phenol ethoxylate based surfactant), Gafac® RE-610 (phosphate ester based surfacatant), sorbitol, tricresyl phosphate, dimethyl sebacate, ethyl glycolate, ethylphthalyl ethyl glycolate, and p-toluene ethyl sulfonamide. Solvents for other adhesives such as carboxymethylcellulose, (CMC), which may be optionally included in the adhesive compositions include mixtures of water and water-miscible solvents such as ethanol and acetone. Solutions of low concentration can be made with up to 40% acetone and/or 50% alcohol. Other solvents which made be used include ethanolamines; ethylene glycol; glycerol; 1,2,6-hexanetriol; mono-, di-, and triacetin; 1,5-pentanediol; polyethylene glycol (molecular weight 600 or less); propylene glycol; and trimethylolpropane.

When the adhesive compositions are prepared by dissolving the adhesive component(s) in water and/or other solvents, various embodiments of the process includes: dissolving the polymers in one or more of the solvents for polymers; dissolving an optional adhesive in a suitable solvent and coating the resulting mixture onto the non-adhesive self-supporting layer and then optionally sifting one or more adhesives onto the coated layer. Coating the layer can be achieved by techniques commonly known in the art including extrusion, doctor blading, spraying, dipping, etc.

After the polymer has been deposited on the layer by one of the means described above, the layer is then dried. Next, the denture adhesive composition is mechanically softened by running it through a ring-roller or micro-cracker or any other suitable means. The composition is then pressed smooth in a hydraulic press or flat-roller or other suitable means. The composition is then die-cut into denture shapes. These shapes may facilitate application of the composition to the dentures.

The following examples further describe and demonstrate embodiments within the scope of the present invention. The examples are given solely for the purpose of illustration and are not to be construed as limitations of the present invention. Many variations of these are possible without departing from the spirit and scope of the invention.

EXAMPLE I (A–G)

The following examples A to G describe various mixed salts and the process for making these mixed salts of AVE/MA polymers:

| Component | A (In Grams) | B (In Grams) | C (In Grams) | D (In Grams) |
|---|---|---|---|---|
| Water | 2844.17 | 2847.7 | 2847.3 | 2844.71 |
| Calcium Hydroxide | 24.2 | 21.36 | 21.07 | 22.78 |
| Zinc Oxide | 10.95 | 10.95 | 10.95 | 12.51 |
| Ferric Sulfate, N-Hydrate | 0.68 | | 0.68 | |
| AVE/MA Anhydride Polymer[1] | 120 | 120 | 120 | 120 |
| Resulting Mixed Salt | Ca(42.5%)/Zn (17.5%)/Fe(0.5%)/FA(39.5%) | Ca (37.5%)/Zn (17.5%)/FA(45%) | Ca(37%)/Zn (17.5%)/Fe (0.5%)/FA(45%) | Ca(40%)/Zn (20%)/FA (40%) |

| Component | E (In Grams) | F (In Grams) | G (In Grams) |
|---|---|---|---|
| Water | 2846.14 | 2845.94 | 2844.63 |
| Calcium Hydroxide | 21.36 | 21.21 | 22.72 |
| Zinc Oxide | 12.51 | 12.51 | 12.51 |
| Ferric Sulfate, N-Hydrate | | 0.34 | 0.14 |
| AVE/MA Anhydride Polymer | 120 | 120 | 120 |
| Resulting Mixed Salt | Ca (37.5%)/Zn (20%)/FA(42.5%) | Ca 37.25%)/Zn (20%)/Fe(0.25 %)/FA(42.5%) | Ca(39.9%)/Zn (20%)/Fe(0.1 %)/FA(40%) |

Weigh the above components and add to a 4 liter reaction vessel while mixing. Use 15% of water to pre-slurry all powders except the AVE/MA. Wash down the residual powders from the wall of the vessel. Then react the mixture at 80 to 95° C. Dry the solution in trays in an oven at 60 to 70° C. Mill all dried flakes to a fine powder. The above polymer salts can be modified by using 12.81 to 27.90 grams of calcium hydroxide, 9.38 to 15.64 grams of zinc oxide, and/or 0 to 3.42 grams of ferric sulfate n-hydrate. Equivalent mixed salts of AVE/MA/IB can be obtained by the same method as above, substituting the AVE/MA/IB for AVE/MA, at various levels.

EXAMPLE II

Denture stabilizing compositions in cream form can be made by blending together the following ingredients:

Gantrez AN 169 available from ISP Corporation, with a specific viscosity of 2.5 to 3.5, and/or AVE/MA copolymer with specific viscosity of 6.3 and/or 7.3.

|  | weight (grams) |
| --- | --- |
| White Mineral Oil | 89.74 |
| Petrolatum,White | 82.01 |
| Carboxymethylcellulose Sodium | 75.00 |
| Silicon Dioxide, Colloidal | 4.28 |
| Colorant (Opatint Red Dye) | 0.23 |
| Any AVE/MA mixed salt of A–G or any AVE/MA/IB mixed salt of A–G | 123.75 |

Weigh, heat and mix the red dye, petrolatum, and mineral oil in a glass jar at 50 to 60° C. until visually uniform. Then weigh and shake-blend the powders (colloidal silicon dioxide, CMC, AVE/MA copolymer mixed salt or AVE/MA/IB mixed salt) together in a container. Thereafter, mix the powders into the liquid with a spatula until visually a uniform pink cream. The above cream can be modified by increasing or decreasing the level of AVE/MA mixed salt or AVE/MA/IB mixed salt by 0 to 18.75 grams, petrolatum by 0 to 18.75 grams, and/or the CMC by 0 to 18.75 grams. The above cream composition can also be modified by using mixtures of the various AVE/MA mixed polymer salts and/or AVE/MA/IB mixed salts. The subject places from 0.1 to 2 grams of the cream composition on the denture. Then the subject inserts the denture into his/her mouth and presses it into place.

EXAMPLE III

Denture stabilizing compositions in powder form can be made by blending together the following ingredients:

|  | weight (grams) |
| --- | --- |
| Carboxymethylcellulose Sodium | 40.00 |
| Any AVE/MA mixed salt of A–G or any AVE/MA/IB mixed salt of A–G | 60.00 |

Blend all components together. The above compositions can be modified by increasing or decreasing the AVE/MA mixed salt or AVE/MA/IB mixed polymer salt by 0 to 50 grams and/or the CMC by 0 to 40 grams. The above powder compositions can also be modified by using mixtures of the various AVE/MA mixed salts and/or AVE/MA/IB mixed salts. The subject places from 0.1 to 2 grams of the composition on a pre-moistened denture, allowing it to hydrate briefly. Then the subject inserts the denture into his/her mouth and presses it into place.

EXAMPLE IV

Denture stabilizing compositions in wafer form can be made by wetting a 58" by 20" non-woven polyester (non-adhesive self-supporting layer) with water. Uniformly coat this wet sheet with the compositions listed below. Thereafter, rewet the layer with water. Dry the layer. Mechanically soften the composition by ring-roller, and then smooth the composition on a hydraulic press. Die-cut the composition into desired shapes. Moisten and apply these wafer compositions to the dentures. Then insert the denture into the mouth and press it into place.

|  | weight (grams) |
| --- | --- |
| Carboxymethylcellulose Sodium | 60.00 |
| Any AVE/MA mixed salt of A–G or any AVE/MA/IB mixed salt of A–G | 90.00 |

These wafer compositions can be modified by increasing or decreasing the AVE/MA mixed polymer salt or AVE/MA/IB mixed polymer salt by 0 to 60 grams and/or carboxymethylcellulose by 0 to 60 grams. The above wafer compositions can also be modified by using mixtures of the various AVE/MA mixed salts and/or AVE/MA/IB mixed polymer salt.

What is claimed is:

1. A denture adhesive composition comprising a mixed salt of a copolymer of alkyl vinyl ether-maleic acid or anhydride, the mixed salt containing a cationic salt function comprising:

a) at least about 22.5% calcium cations;

b) from about 15% to about 25% zinc cations;

c) from 0% to about 2.5% of a cation selected from the group consisting of iron, boron, aluminum, vanadium, chromium, manganese, nickel, copper, yttrium, titanium, and mixtures thereof; and d) from about 36% to about 50% free acid component; wherein when the composition is in the form of a cream or wafer; wherein the free acid constitutes the unreacted carboxyl groups of the copolymer; and wherein the specific viscosity of the starting acid or anhydride copolymer is from 2.5 to 3.5.

2. The denture adhesive composition according to claim 1 wherein the level of calcium cations is from about 22.5% to about 49%.

3. The denture adhesive composition according to claim 2 wherein the level of calcium cations is from about 23.5% to about 48%.

4. The denture adhesive composition according to claim 1 wherein the level of zinc cations is from about 16% to about 24%.

5. The denture adhesive composition according to claim 4 wherein the level of zinc cations is from about 18% to about 22%.

6. The denture adhesive composition according to claim 1 wherein the level of iron cations is from about 0.01% to about 2%.

7. The denture adhesive composition according to claim 1 further comprising one or more ingredients selected from the group consisting of additional adhesive components, plasticizers, colorants, preservatives, thickeners, vehicles, flavors, fragrances, sensates, and mixtures thereof.

8. The denture adhesive composition according to claim 7 wherein the additional adhesive component is selected from the group consisting of natural gums, synthetic polymers, mucoadhesive polymers, hydrophilic polymers, hydroxyethylcellulose, hydroxypropylcellulose, hydroxypropyl-methyl-cellulose, sodium carboxymethylcellulose, mixed salts of alkyl vinyl ether-maleic acid copolymers, alkyl vinyl ether-maleic acid copolymers, alkyl vinyl either-maleic anhydride copolymers, and mixtures thereof.

9. A denture adhesive composition according to claim 7 wherein the vehicle is selected from the group consisting of petrolatum, liquid petrolatum, mineral oil, and glycerin.

\* \* \* \* \*